(12) United States Patent
Yao

(10) Patent No.: US 8,684,172 B2
(45) Date of Patent: Apr. 1, 2014

(54) ANALYTE SENSOR CONTAINER SYSTEMS WITH SENSOR ELEVATOR AND STORAGE METHODS

(75) Inventor: Raymond Yao, Ossining, NY (US)

(73) Assignee: Bayer Healthcare LLC, Whippany, NJ (US)

( * ) Notice: Subject to any disclaimer, the term of this patent is extended or adjusted under 35 U.S.C. 154(b) by 242 days.

(21) Appl. No.: 13/130,651

(22) PCT Filed: Nov. 18, 2009

(86) PCT No.: PCT/US2009/064963
§ 371 (c)(1),
(2), (4) Date: May 23, 2011

(87) PCT Pub. No.: WO2010/065309
PCT Pub. Date: Jun. 10, 2010

(65) Prior Publication Data
US 2011/0247949 A1    Oct. 13, 2011

Related U.S. Application Data

(60) Provisional application No. 61/119,365, filed on Dec. 2, 2008.

(51) Int. Cl.
*B65D 81/26* (2006.01)
*A61B 17/06* (2006.01)
*B65G 59/00* (2006.01)
*B65B 7/28* (2006.01)
*A61B 19/02* (2006.01)
*B65D 83/08* (2006.01)

(52) U.S. Cl.
CPC ............. *B65D 81/264* (2013.01); *A61B 19/026* (2013.01); *B65D 83/0858* (2013.01)

USPC .......................................................... 206/204

(58) Field of Classification Search
CPC . B65D 81/264; B65D 83/0858; A61B 19/026
USPC ......... 206/204, 438, 528, 538, 540, 817, 825; 53/471; 220/529; 221/244, 296; 422/401, 405
See application file for complete search history.

(56) References Cited

U.S. PATENT DOCUMENTS 2,944,661 A * 7/1960 Goldstein ...................... 206/5.1
3,717,282 A * 2/1973 Nordskog ....................... 221/279
(Continued)

FOREIGN PATENT DOCUMENTS

WO    WO 2010/065307    6/2010

OTHER PUBLICATIONS

International Search Report and Written Opinion of International Application No. PCT/US2009/64963 dated Mar. 4, 2010.

(Continued)

*Primary Examiner* — Luan K Bui
(74) *Attorney, Agent, or Firm* — Dugan & Dugan, PC

(57) ABSTRACT

An analyte sensor container system is provided for storing and dispensing analyte sensors. The analyte sensor container system includes a container body having a moveable member received therein. The moveable member may have one or more compartments with one or more analyte sensors supported thereon and a lid hinged to the container body. An elevator mechanism causes relative movement between the container body and moveable member upon opening and closing the lid. As such, the one or more analyte sensors are readily accessible to a user when the lid is opened, and retract into the container body upon lid closure. Methods of storing analyte sensors are provided as are numerous other aspects.

15 Claims, 3 Drawing Sheets

(56) References Cited

U.S. PATENT DOCUMENTS

| | | | |
|---|---|---|---|
| 4,771,887 A * | 9/1988 | Nehl | 206/387.15 |
| 6,136,352 A * | 10/2000 | Silverstein et al. | 426/115 |
| 6,378,702 B1 * | 4/2002 | Kintzig | 206/817 |
| 7,501,093 B2 * | 3/2009 | Demelo et al. | 422/526 |
| 8,236,254 B2 * | 8/2012 | Myles et al. | 206/204 |
| 8,388,905 B2 * | 3/2013 | Neel et al. | 206/528 |
| 2003/0223906 A1 | 12/2003 | MCallister et al. | |
| 2004/0007585 A1 * | 1/2004 | Griffith et al. | 221/232 |
| 2007/0264165 A1 * | 11/2007 | Chan et al. | 422/104 |
| 2008/0257905 A1 * | 10/2008 | Giraud et al. | 221/296 |
| 2011/0226643 A1 * | 9/2011 | Kates et al. | 53/471 |

OTHER PUBLICATIONS

International Preliminary Report on Patentability of International Application No. PCT/US2009/64963 dated Jun. 16, 2011.

* cited by examiner

ANALYTE SENSOR CONTAINER SYSTEMS WITH SENSOR ELEVATOR AND STORAGE METHODS

The present application claims priority to U.S. Provisional Patent Application No. 61/119,365 filed Dec. 2, 2008, and entitled "ANALYTE SENSOR CONTAINER SYSTEMS WITH SENSOR ELEVATOR AND STORAGE METHODS" which is hereby incorporated herein by reference in its entirety for all purposes.

FIELD OF THE INVENTION

The present invention relates to systems and methods for packaging and dispensing analyte sensors that may be used to detect an analyte concentration level in a bio-fluid sample taken from a patient.

BACKGROUND OF THE INVENTION

The monitoring of an analyte concentration level in a bio-fluid may be an important part of health diagnostics. For example, an electrochemical analyte sensor may be employed for monitoring of a patient's blood glucose level as part of diabetes treatment and care. Furthermore, analyte sensors may be used for testing of total cholesterol, uric acid, lipids, triglycerides, high-density lipoprotein (HDL), low-density lipoprotein (LDL), etc.

In analyte monitoring, after a bio-fluid sample (e.g., blood) has been obtained from the patient, such as by the use of a lancet, the bio-fluid sample may then be transferred to a medium (e.g., an analyte sensor test strip) for measurement of the sample's analyte concentration level. The analyte sensor test strip may be received in a testing meter and a display of a measured analyte level may be provided. In the case of glucose monitoring, the meter is sometimes be referred to as a "glucose meter." For user's whom test frequently, storage and retrieval of the analyte test sensors may be important, as is providing accurate measurement of an analyte concentration level in the bio-fluid sample. It therefore may be beneficial to provide systems and methods, which may aid in the storage and retrieval, and/or measurement accuracy of such analyte sensors.

SUMMARY OF THE INVENTION

In a first aspect, the present invention provides an analyte sensor container system including a container body; a moveable member slidably received in the container body and supporting at least one analyte sensor; a lid hinged to the container body; and an elevator mechanism adapted to elevate the moveable member and the at least one analyte sensor relative to the container body upon opening the lid.

In another aspect, the present invention provides an analyte sensor container system including a container body including a recess; a moveable member slidably received in the recess, the moveable member including a plurality of compartments each containing at least one analyte sensor; a lid hinged to the container body; and an elevator mechanism including a spring biasing the moveable member and an elevator post contacting the lid wherein the elevator mechanism is adapted to elevate the moveable member and the analyte sensors relative to the container body upon opening the lid.

In a method aspect, a method of storing analyte sensors is provided including the steps of providing a container having a container body and a hinged lid, the container body having a moveable member slidably moveable therein; supporting one or more analyte sensors on the moveable member; and closing the lid thereby resultantly causing the moveable member to move into the container body and retract the one or more analyte sensors relative to the container body.

Other features and aspects of the present invention will become more fully apparent from the following detailed description, the appended claims and the accompanying drawings.

DETAILED DESCRIPTION

In the measurement of analyte concentration levels, an accuracy of an analyte sensor (e.g., an analyte sensor test strip) may be important. As such, the analyte sensors (e.g., test strips) may be provided in a sealed package (such as a sealed foil package or pouch) in an attempt to protect the sealed sensors from environmental exposure (e.g., humidity and/or temperature), at least until they are opened. However, the packages may contain 10 or more analyte sensors (e.g., test strips) and once the package has been opened, the individual loose sensor strips contained therein may be undesirably exposed to the environment. The length of time a particular test strip is exposed may vary, depending on the testing level of the user and other factors. However, in some instances, extended environmental exposure may affect the properties and, therefore, possibly an accuracy of the analyte sensors. In particular, an analyte sensor reading may be somewhat affected by high or low humidity levels and/or exposure to relatively large temperature variations, for example. Moreover, once opened, the analyte sensors may be misplaced for a time or even mixed with other sensor strips from other opened packages, possibly exacerbating the length of time and amount of environmental exposure.

Further, once opened, it would be desirable that the sensor strips may be readily accessible by the user. As such, the present invention may help with organization, storage and accessibility of the analyte sensors and additionally may limit a length and/or severity of exposure of the analyte sensors to the environment.

Therefore, according to one aspect of the present invention, a sealed analyte sensor container system is provided which includes a moveable member supporting one or more analyte sensors. One or more compartments containing one or more analyte sensors (or packages of sensors) may be provided in the moveable member. The moveable member may be spring biased relative to a container body. In operation, as a lid of the container is opened, the moveable member and the one or more analyte sensors may be elevated relative to the container body by the action of the spring bias provided to the moveable member. Thus, the packaged sensors and any opened (loose) analyte sensors may be raised/elevated relative to the container body, such that the analyte sensors may be readily accessible (e.g., grasped) by a user. In particular, one or more of the analyte sensors may be elevated such that a top portion of the one or more of the sensors may extend above a top edge of the container body. Upon closing the lid, the moveable member and, resultantly, the analyte sensors retract into the container body.

These and other embodiments are described below with reference to FIGS. 1-5.

Figure 1:
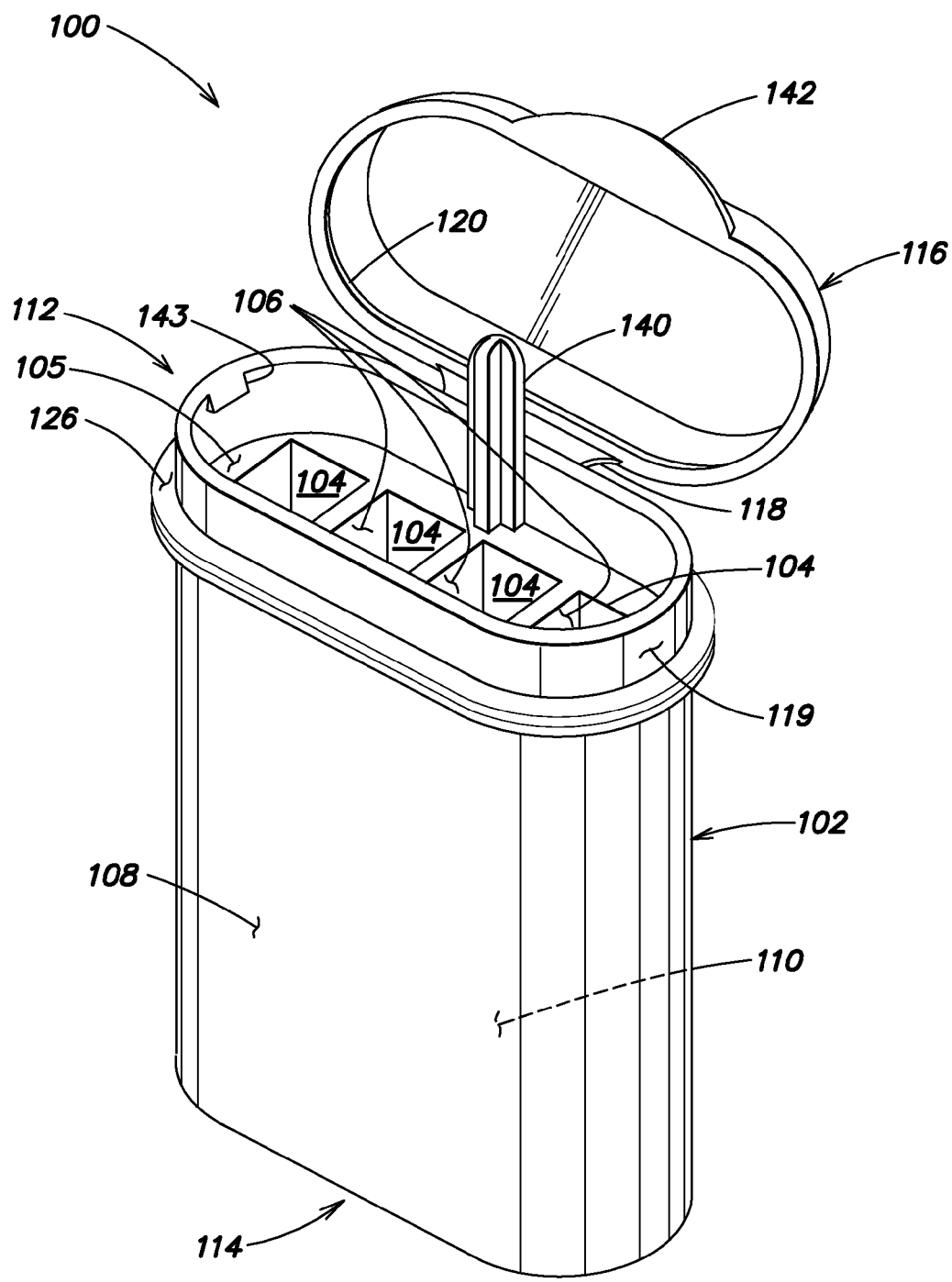
FIG. 1 is a perspective view of an exemplary embodiment of an analyte sensor container system provided according to the present invention.
Figure 3:
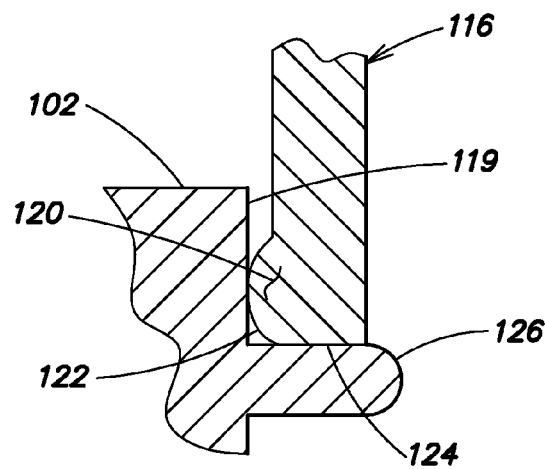
FIG. 3 is an enlarged partial cross-sectioned view of a sealing portion of an exemplary embodiment of an analyte sensor container system of FIG. 2 according to aspects of the present invention.
Figure 4:
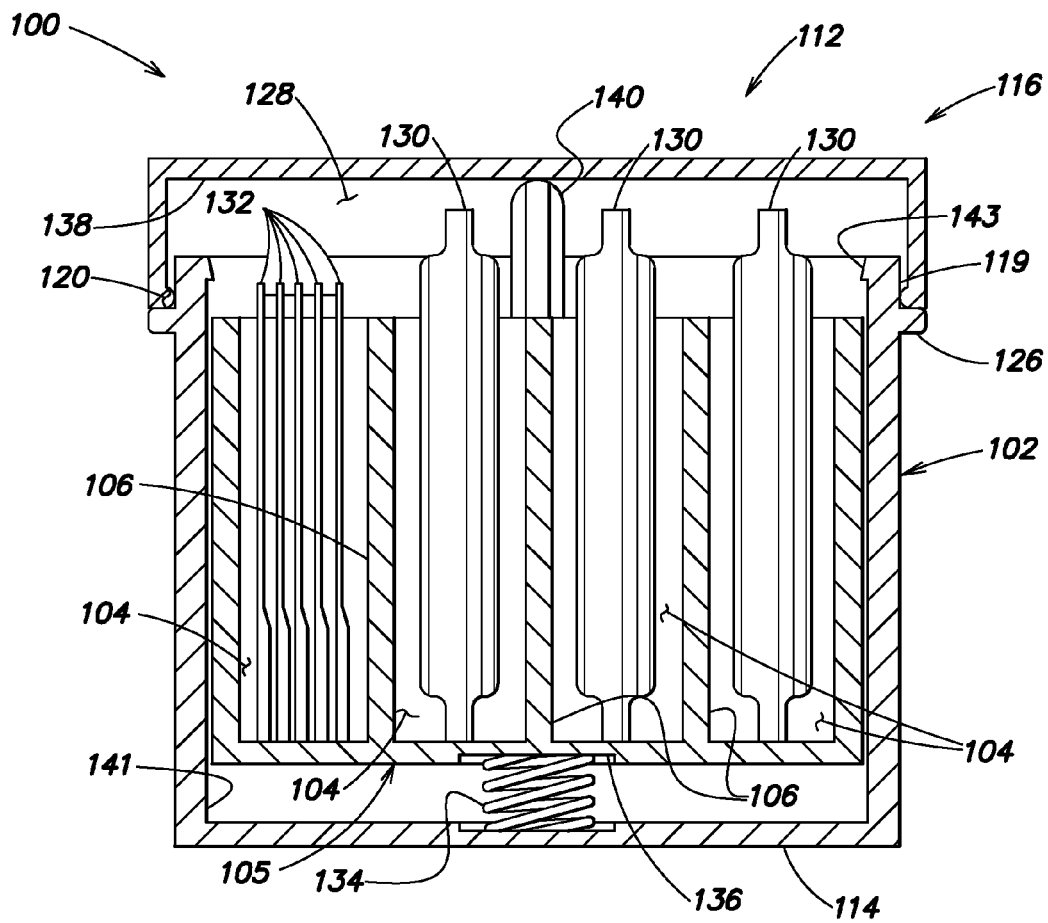
FIG. 4 is a cross-sectioned front view of an exemplary embodiment of an analyte sensor container system of FIG. 1 shown in a closed configuration.
Figure 5:
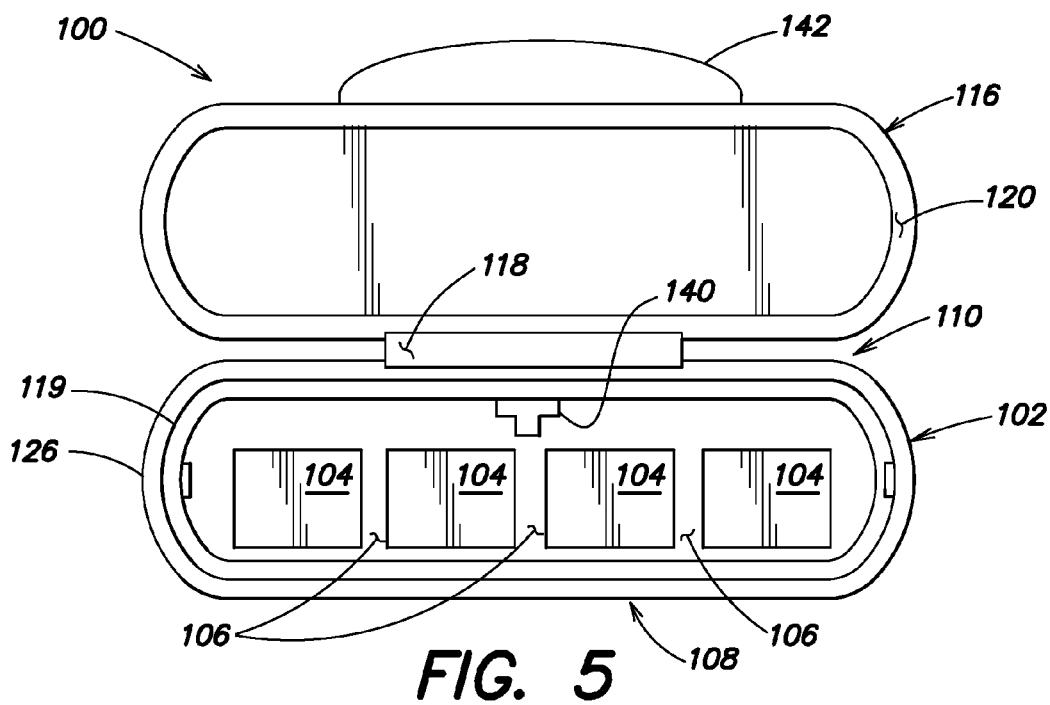
FIG. 5 is a top plan view of an exemplary embodiment of an analyte sensor container system of FIG. 1 shown in the opened configuration with the analyte sensors not shown for clarity.

FIGS. 1-5 illustrate various views of an exemplary embodiment of an analyte sensor container system 100 provided according to the present invention. The analyte sensor container system 100 may include a container body 102, which may have an oval shape in a top plan view, for example. Other shapes may be used, such as rectangular, irregular hexagonal or octagonal, racetrack, or other like shapes. The body 102 may include a moveable member 105 received therein which may be adapted for supporting one or more analyte sensors (see FIGS. 2 and 4). FIGS. 1 and 5 have the analyte sensors removed for clarity.

Figure 2:
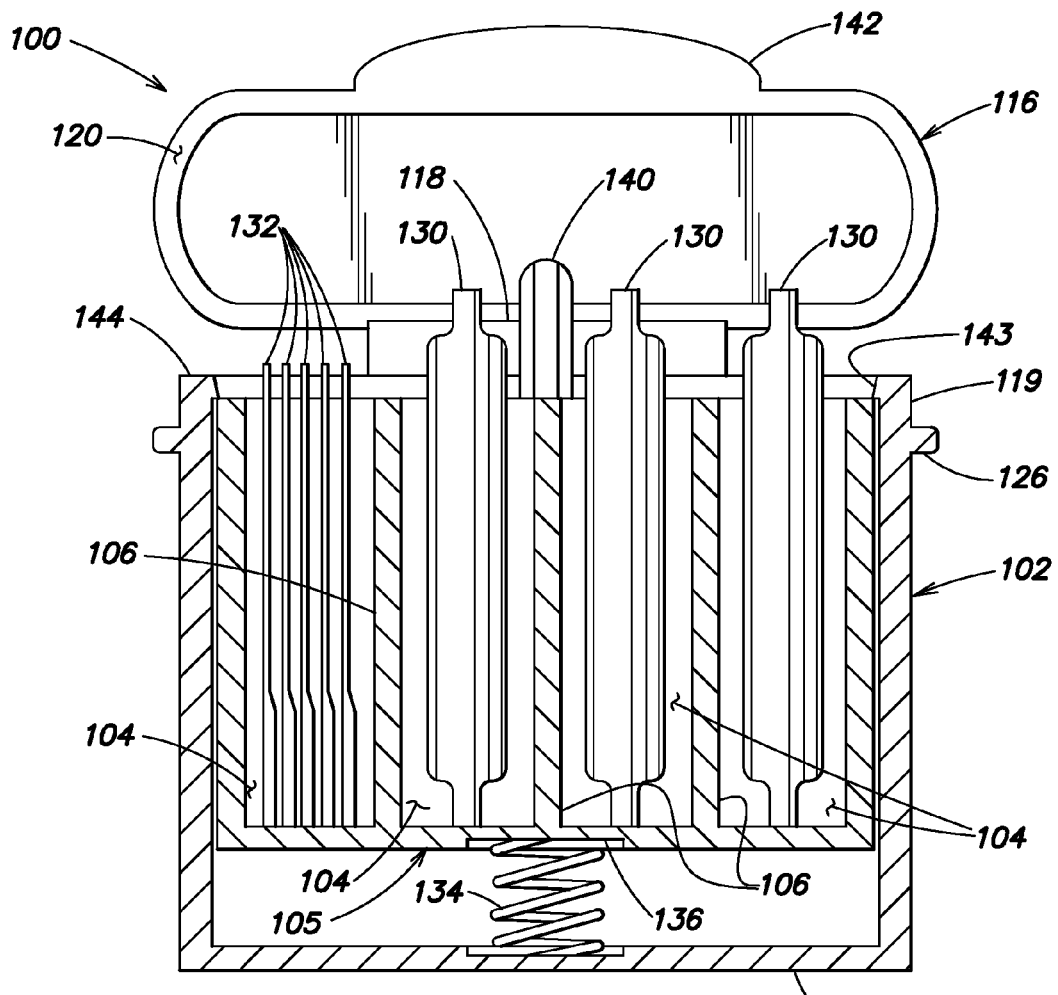
FIG. 2 is a cross-sectioned front view of an exemplary embodiment of an analyte sensor container system of FIG. 1 shown in an opened configuration.

In the depicted embodiment, the moveable member 105 may include one or more compartments 104 formed therein. Each compartment 104 may have a length (depth) longer than a width thereof. In some embodiments, the depth of at least one compartment 104, and preferably all compartments, in the moveable member 105 is less than a length of the at least one analyte sensor. The compartments 104 may have any cross-sectional shape such as a square or a rectangle suitable to contain the analyte sensors in an upright orientation, as shown in FIG. 2. Other compartment shapes may be used. The compartments 104 may be separated from each other by partition walls 106, for example. The partition walls 106 may extend in a straight line from a front 108 to a back 110 of the container body 102 and may also extend in a straight line from a top 112 to a bottom 114 of the moveable member 105 (See FIG. 1). The partition walls 106 may optionally include a curvature.

A lid 116 may be attached to the container body 102 and may form a generally substantially airtight seal therewith. The lid 116 may be attached to a back 110 and top 112 of the container body 102, such by a suitable hinge 118. The hinge 118 may be formed as a thin bridge of flexible polymer material during molding of the container body 102 and lid 116, for example. Other types of suitable hinges may be provided, such as a snap on hinge, which has features, which snap onto a mating feature formed on the body 102. The lid 116 may be of approximately a same size and shape (in top plan view) as an outer peripheral surface 119 of the container body 102 at its top 112. To form a generally air-tight seal, a lip 120 may be provided on an inside surface of the lid 116 and may be adapted to be received in contact with the outer peripheral surface 119 of the container body 102 as best shown in FIG. 3. The lip 120 may extend radially inward by a short distance (about 0.5 mm to 3 mm) from a bottom portion of the lid 116 and may include a sealing portion 122 which may be radiused, and which may contact and seal against the outer surface 119. In a closed orientation (as shown in FIGS. 3 and 4), a lower edge 124 of the lid 116 may abut in a vertical direction against a lid stop 126 which may extend radially outward from the container body 102 and may extend at least partway around the body 102, and preferably all the way around the body 102.

Thus, it should be recognized that the lid 116 and body 102 cooperate to form a resealable chamber 128 (FIG. 4) within which the unopened packages of analyte sensors 130 (which may contain several analyte sensors sealed in a foil pouch member, for example) and/or loose sensors 132 (e.g., from opened packages) may be stored and contained. The container body 102, lid 116, and hinge 118 may be formed of any suitable injection-molded plastic, for example, a thermoplastic material such as polyolefin, polycarbonate, or polyamide. The moveable member 105 may be made of a same or different material as the container body 102 and lid 116. Additionally, as will be described more fully below, the re-sealable chamber 128 may include a desiccant material in communication with any loose sensors 132 to limit a length of time and/or severity of environment exposure thereof.

To cause an elevation of the moveable member 105 relative to the container body 102 upon opening the lid 116, a spring 134 or other biasing member may be provided, as shown in FIGS. 2 and 4. Mounted between the container body 102 and the movable member 105, the spring 134 may spring bias the movable member 105 relative to the container body 102. In particular, the spring 134 which may be a compression spring, leaf spring, washer spring, or any other suitable spring type, may engage between a portion (e.g., a bottom) of the container body 114 and a portion (e.g., bottom 136) of the moveable member 105 (as shown in FIGS. 2 and 4).

In FIG. 4, the container system 100 is shown with the lid 116 in a closed and sealed configuration. In the sealed configuration, with the lid 116 in a closed position, an underside of the lid 138 contacts an elevator post 140 which extends from a body of the moveable member 105. During lid closure, the underside 138 of the lid 116 contacts the end of the elevator post 140 and causes the moveable member 105 to slide downwardly in a recess 141 provided in the container body 102. This lid motion flexes and compresses the spring 134 coupled between the moveable member 105 and the container body 102. The spring 134 is shown in a compressed state in FIG. 4. The elevator mechanism is operative between an open position and a closed position wherein in the closed position the at least one analyte sensor is entirely housed within the container body 102 with the lid 116 closed. The elevator post 140 may include a rounded end adapted to engage the lid, to reduce friction and provide for smooth closing/opening. The elevator post 140 may be formed integrally with the moveable member 105, or otherwise mechanically attached thereto.

Upon opening the container system 100 by a user pushing up on a tab 142 (FIGS. 1, 2 and 5) of the lid 116 with a finger or thumb, for example, the force of the spring 134 may extend and push the moveable member 105 upwardly relative to the body 102. The system 100 is shown in a fully open condition in FIG. 2 whereby one or more stops 143 may limit the upward motion of the moveable member 105 relative to the container body 102. The stops 143 may be of a size such that the moveable member 105 may be installed through a slight deflection of the side walls of the container body 102, yet the stops 143 delimit the upward motion of the member 105 when installed in the body 102. In this condition, the user may readily access the packaged or loose sensors 130, 132, respectively. In particular, the top ends of the packages 130 and/or loose analyte sensors 132 may be raised above an upper edge 144 of the container body 102 (see FIG. 2) such that they are readily accessible and may be readily grasped by the user.

In operation, once the user has opened the packaged sensors 130 to remove a single sensor for testing, the user may reseal the resealable chamber 128 (FIG. 4) by pushing on the lid 116 and causing the lid to seal against the container body 102. At the same time, pushing on the lid 116 causes the moveable member 105 to move downward and slide within the container body 102. This movement retracts the sensor packages 130 and loose sensors 132 into the container body 102 thereby limiting exposure to the environment of the remaining loose, unused sensors 132.

In an alternative embodiment, the moveable member may support the analyte sensors and may comprise a platform having the post extending therefrom. A grid-like member may be provided at the top of the container body and the sensor and/or packages of sensors may slide within pockets formed in the grid-like member. The grid-like member serves the function of compartmentalizing the analyte sensors, which allows access to the ends of the sensors/packages of sensor 130 as the moveable member is elevated upon opening the lid 116.

Each of the aforementioned system embodiments may include a desiccant or hydrophilic material in communication with re-sealable chamber 128 and the loose analyte sensors 132. For example, the desiccant material may be provided in the container body 102 or under the lid 116. Optionally, the desiccant material may be provided within the moveable member 105, the compartments 104 such as at a bottom of the compartments or provided as part of the walls of the compartments 104, or may be a part of the elevator post 140. The desiccant material may be a silica gel, clay, or molecular sieve material, for example. In some embodiments, the desiccant material may be a desiccant plastic molded into the container body 102, moveable member 105, walls of the compartments 104, lid 116, or elevator post 140, for example. Plastic desiccants are described in U.S. Pat. Nos. 5,911,937; 6,080,350; 6,124,006 and 6,130,263 for example. The desiccant may help further limit environment exposure to any loose sensors 132.

The foregoing description discloses only exemplary embodiments of the invention. Modifications of the above-disclosed analyte sensor container system, which fall within the scope of the invention, will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. An analyte sensor container system, comprising:
   a container body;
   a moveable member slidably received in the container body and supporting at least one analyte sensor, wherein the container body includes at least one stop to limit an upward motion of the moveable member relative to the container body;
   a lid hinged to the container body, the lid including a lip adapted to provide a substantially air-tight seal against a peripheral surface of the container body; and
   an elevator mechanism adapted to elevate the moveable member and the at least one analyte sensor relative to the container body upon opening the lid wherein the elevator mechanism includes an elevator post that projects from the moveable member that is configured to contact the lid while opening and closing the lid.

2. The analyte sensor container system of claim 1 wherein the elevator mechanism includes a spring coupled between the container body and the moveable member.

3. The analyte sensor container system of claim 1 wherein the post includes a rounded end adapted to engage the lid.

4. The analyte sensor container system of claim 1 wherein the elevator mechanism includes a spring that contacts a bottom of the moveable member and a bottom of the container body.

5. The analyte sensor container system of claim 1 wherein the lid is hinged to the container body by a bridge of molded material.

6. The analyte sensor container system of claim 1, further comprising a tab extending from the lid.

7. The analyte sensor container system of claim 1 wherein the elevator mechanism is operative between an open position and a closed position wherein in the closed position the at least one analyte sensor is entirely housed within the container body with the lid closed.

8. The analyte sensor container system of claim 1 wherein the moveable member includes a plurality of compartments each containing at least one analyte sensor.

9. The analyte sensor container system of claim 1 wherein the container body includes a lid stop to which the lid abuts upon closure.

10. The analyte sensor container system of claim 1 wherein a depth of at least one compartment in the moveable member is less than a length of the at least one analyte sensor.

11. The analyte sensor container system of claim 1 wherein a desiccant material is provided in communication with a resealable chamber formed by the container body and the lid.

12. An analyte sensor container system, comprising:
   a container body including a recess;
   a moveable member slidably received in the recess, the moveable member including a plurality of compartments each containing at least one analyte sensor, wherein the container body includes at least one stop to limit an upward motion of the moveable member relative to the container body;
   a lid hinged to the container body the lid including a lip configured to provide a substantially air-tight seal against a peripheral surface of the container body; and
   an elevator mechanism including a spring biasing the moveable member and an elevator post contacting the lid wherein the elevator mechanism is adapted to elevate the moveable member and the analyte sensors relative to the container body upon opening the lid.

13. A method of storing analyte sensors, comprising the steps of:
   providing a container having a container body and a hinged lid, the container body including an elevator mechanism including a moveable member slidably moveable in the container body, the elevator mechanism including an elevator post that projects from the moveable member that is configured to contact the hinged lid while opening and closing the hinged lid;
   supporting one or more analyte sensors on the moveable member, wherein the container body includes at least one stop to limit an upward motion of the moveable member relative to the container body; and
   closing the lid, the lid having a lip to engage a container peripheral surface of the container body providing a substantially air-tight seal and thereby resultantly causing the moveable member to move into the container body and retract the one or more analyte sensors relative to the container body.

14. The method of storing analyte sensors of claim 13 wherein the closing of the lid causes flexure of a spring coupled between the moveable member and the container body.

15. The method of storing analyte sensors of claim 13 wherein one or more compartments are formed in the moveable member.

* * * * *